United States Patent [19]

Jemmott

[11] Patent Number: 5,352,201

[45] Date of Patent: Oct. 4, 1994

[54] COMPACT UNIFORM PRESSURE INFUSION APPARATUS

[75] Inventor: Gilbert F. Jemmott, San Marcos, Calif.

[73] Assignee: Block Medical, Inc., Carlsbad, Calif.

[21] Appl. No.: 191,429

[22] Filed: Feb. 3, 1994

[51] Int. Cl.5 .............................................. A61M 5/148
[52] U.S. Cl. .................................... 604/131; 604/153
[58] Field of Search .............. 604/131, 132, 141, 133, 604/153

[56] References Cited

U.S. PATENT DOCUMENTS

| | | | |
|---|---|---|---|
| 4,221,219 | 9/1980 | Tucker | 604/141 |
| 4,525,164 | 6/1985 | Loeb et al. | 604/131 |
| 4,573,992 | 3/1986 | Marx | 604/141 |
| 4,601,707 | 7/1986 | Albisser et al. | 604/131 |
| 4,626,244 | 12/1986 | Reinicke | 604/141 |
| 4,685,902 | 8/1987 | Edwards et al. | 604/153 |
| 4,772,263 | 9/1988 | Dorman et al. | 604/132 |
| 4,886,499 | 12/1988 | Cirelli et al. | 604/141 |
| 4,955,861 | 9/1990 | Enegren et al. | 604/141 |
| 5,061,242 | 10/1991 | Sampson | 604/141 |
| 5,135,497 | 8/1992 | Hiessel | 604/132 |
| 5,176,644 | 1/1993 | Srasathapat et al. | 604/141 |

Primary Examiner—Paul J. Hirsch
Attorney, Agent, or Firm—Bajer, Maxham, Jester & Meador

[57] ABSTRACT

A liquid infusion apparatus includes an elongated elastic sleeve stretch mounted on a spiral support member within a housing to enable it to expand naturally to maintain a substantially constant pressure over the infusion period.

26 Claims, 4 Drawing Sheets

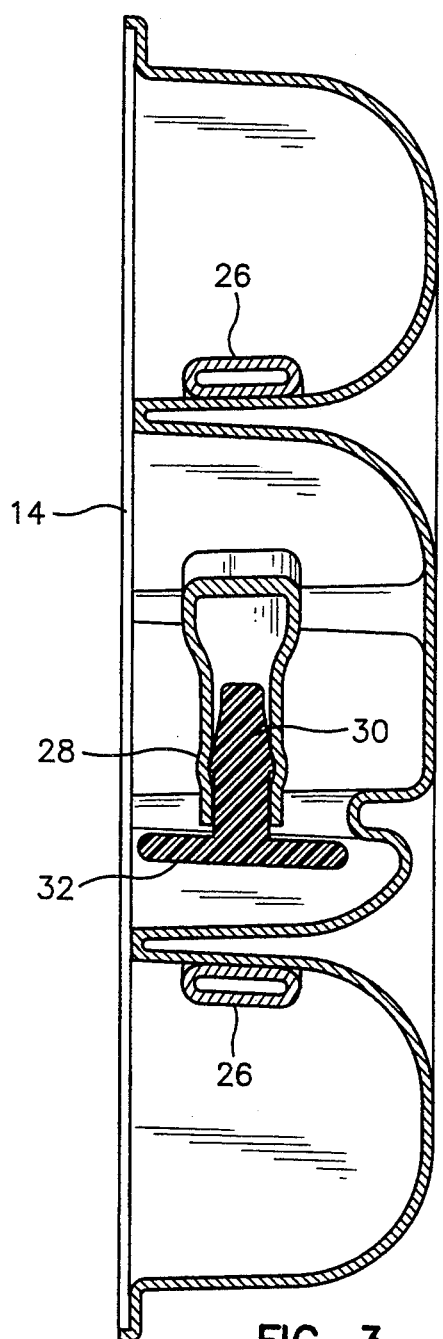
FIG. 3
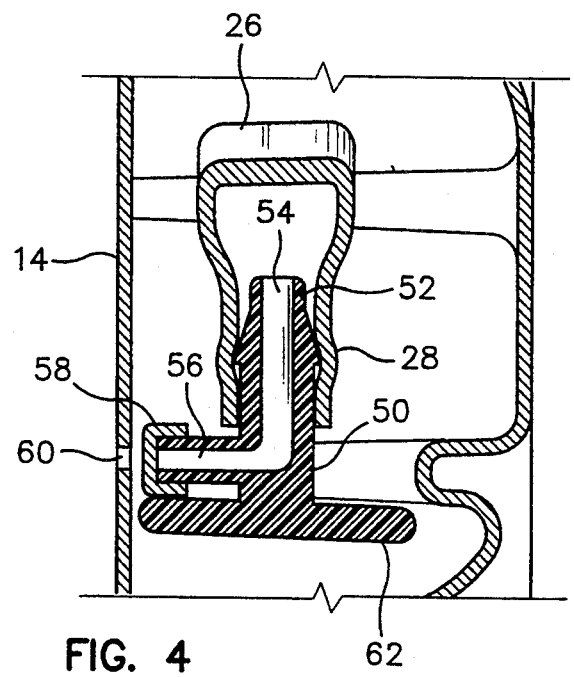
FIG. 4
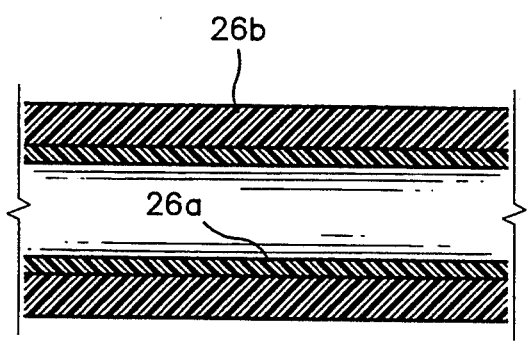
FIG. 5
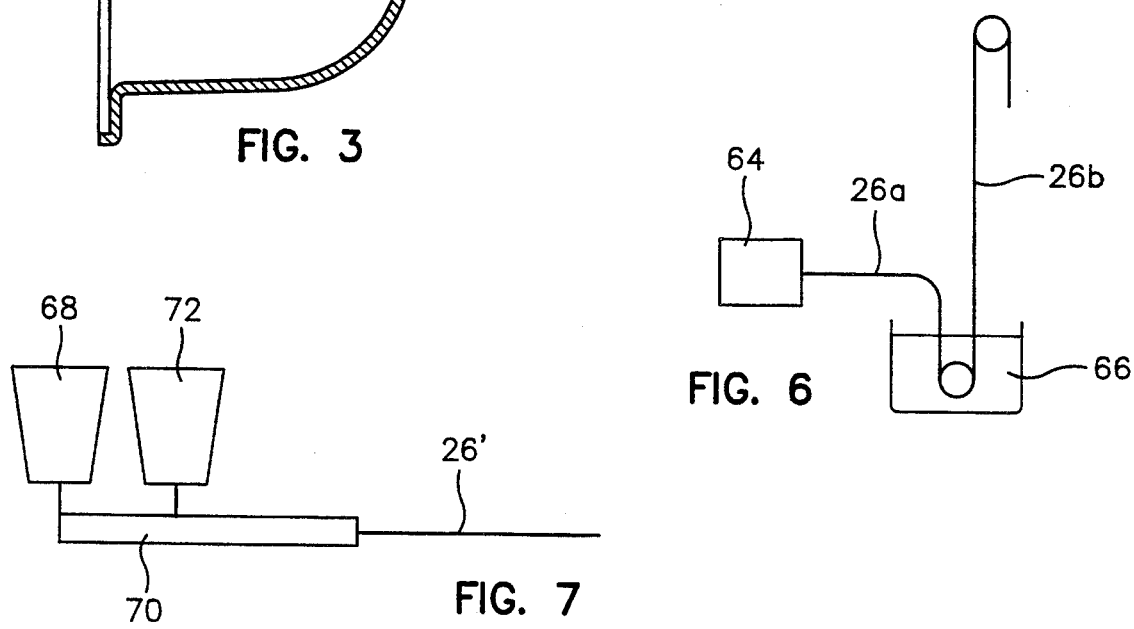
FIG. 6
FIG. 7

COMPACT UNIFORM PRESSURE INFUSION APPARATUS

BACKGROUND OF THE INVENTION

The present invention relates to liquid dispensing apparatus and pertains particularly to an improved infusion apparatus for delivering intravenous drugs at a controlled rate to a patient.

It is often necessary to intravenously supply patients with pharmaceutically active liquids over a long period of time at a controlled rate. In many instances it is desirable that this be accomplished while the patient is in an ambulatory state. A few devices have been developed in the past for accomplishing this purpose.

The prior art devices typically comprise an elastic bladder forming a liquid container mounted in an elongated cylindrical housing, and having a flow control valve or device and tubing for supply of the liquid to the patient. The elastic walls of the bladder expand along the walls of the cylindrical housing when filled with the liquid, and provide the pressure for expelling the liquid. These prior art devices are typically filled by hand by means of a syringe which often requires an inordinate amount of force.

Another drawback to these prior art devices is that the bladder is forced to expand into an unnatural elongated configuration along the housing walls as the container is filled. As a result of this unnatural configuration, the pressure of the bladder varies widely with the volume of liquid therein. Therefore, they do not have a reasonably stable pressure and flow rate over the infusion period.

Most of such devices either have a flow rate that decreases with pressure, which decreases with volume, or one that remains roughly constant until the end where it surges. Attempts have been made to control pressure and flow rates by means of complicated and expensive flow control valves and devices. Other approaches have utilized exotic and expensive elastic materials in an effort to control the pressures and flow rates.

Recent developments as disclosed in U.S. Pat. No. 5,080,652 entitled Infusion Apparatus issued to Sancoif et al, and U.S. Pat. No. 5,105,983 entitled Infusion Apparatus issued Apr. 21, 1992 to Sancoif et al and assigned to the Assignee hereof have overcome many of the problems of the prior art. However, these have some drawbacks, namely they are undesirably bulky for some applications.

It is desirable that an improved infusion device be available that overcomes the above problems of the prior art. More specifically it is desirable that a compact infusion device be available wherein the pressure and flow rate are reasonably constant over the infusion period.

SUMMARY OF THE INVENTION

It is the primary object of the present invention to provide an improved liquid infusion apparatus.

It is another object of the present invention to provide a compact infusion device wherein the pressure and flow rate are reasonably constant over the infusion period. In accordance with a primary aspect of the present invention, a liquid infusion apparatus comprises an elastic reservoir .mounted on a spiral support within a chamber and enabled to expand and contract at a substantially constant pressure.

BRIEF DESCRIPTION OF THE PREFERRED EMBODIMENTS

The above and other objects and advantages of the present invention will become apparent from the following description when read in conjunction with the accompanying drawings wherein:

FIG. 3 is a view taken generally on line 3—3 of FIG. 2;

FIG. 4 is a detailed partial view of a modification of the embodiment of FIG. 1;

FIG. 5 is a detailed sectional view of the elastic bladder FIG. 2;

FIG. 6 is a schematic illustration of apparatus and process for making the bladder of FIG. 5;

FIG. 7 is a schematic illustration of apparatus and process for making an alternate embodiment of the bladder of FIG. 5;

DETAILED DESCRIPTION OF THE PREFERRED EMBODIMENTS

Figure 1:
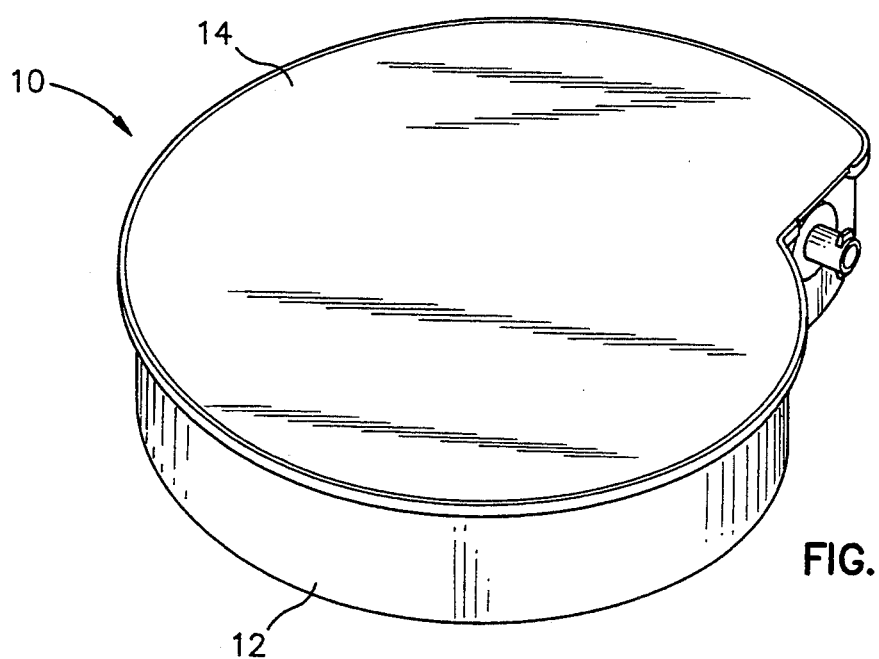
FIG. 1 is a perspective view of an exemplary embodiment of the invention.

Referring to FIG. 1 of the drawings, an exemplary embodiment of an infusion device in accordance with the preferred embodiment of the invention is illustrated and designated generally by the numeral 10. The infusion apparatus is embodied in a housing having a generally flat spiral configuration. However, it may have other outer configurations such as circular, semicircular or square. The apparatus in the illustrated embodiment compromises a main housing comprising thermally formed walls extending upward from a bottom and extending in a radially outward spiral to a terminal end wherein all the connections are provided, as will be explained. The main housing has an open top formed for receiving a generally flat planer cover 14. The cover 14 may be formed with recesses or other structural configurations to enable stacking of a plurality of the units.

Figure 2:
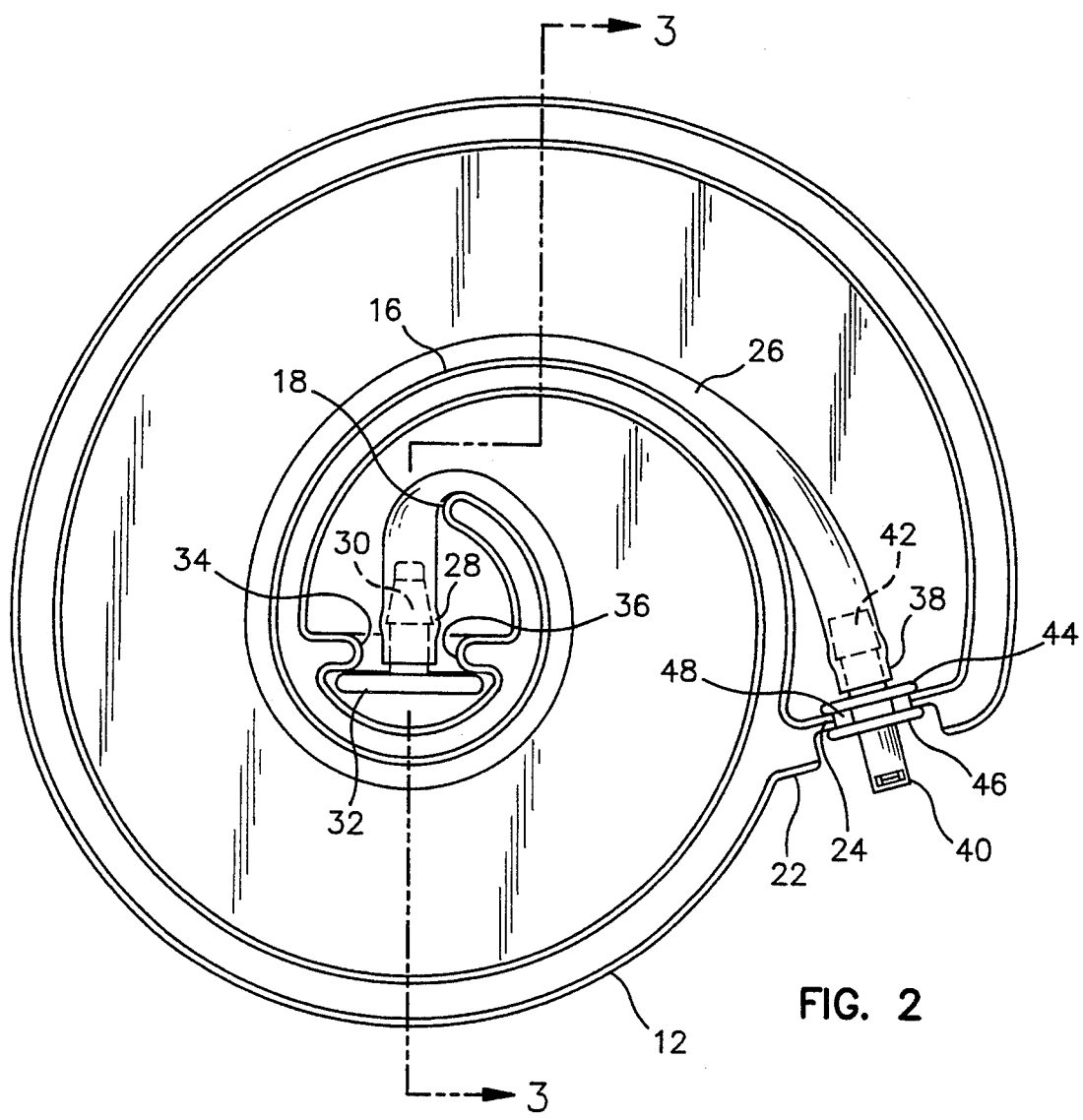
FIG. 2 is a top plan view of the embodiment of FIG. 1 with the cover removed.

The housing is preferably formed of any one of a number of thermoformable plastic polymer materials and vacuum formed into its shape or configuration. Either the housing 12 or the cover 14 or both may be of a transparent material. Preferably at least one is transparent in order to enable viewing the components in the interior of the housing. They may also be formed together of the same material with an integral hinge connection as will be explained. Referring to FIG. 2, the main housing is shaped to form a spiral bladder support and chamber from a central point of the housing spiraling outward to the terminal outlet face of the housing. The housing is formed of an inner wall 16 beginning at an inner end 18 proximate the center of the housing and spiraling outward in a radially outwardly spiral to become an outer wall 20 and continue to a terminal end 22, joining the outer surface or portion thereof and forming a terminal wall 24. The angle subtended by the spiral is preferably between about ¾ turn and 2 turns.

The inner wall 16 forms a spiral support structure for supporting an elongated elastic tubular member 26 forming an elastic bladder or reservoir. The coils of the elastic tube are supported in a common plane and spiral radially outward. The elastic tube or member 26 is preferably pre-stretched up to about 30% with an inner end 28 secured on a barbed plug 30 having a shoulder 32. The shoulder 32 is positioned behind shoulders formed by inner extending wall portions 34 and 36 forming a receptacle for receipt of the plug 30. The elastic tube or member is stretched and bends across the inner end 18 or wall of mounting member 16 and lies compressed substantially flat, as it extends along the wall to an outlet end 38 connected to an outlet connector and valve assembly including a suitable coupling or connector such as a luer connector 40.

The housing of the valve and connector assembly is of a tubular configuration with an inner barbed connector 42 over which an outer end 38 of elastic tube 26 is mounted. The housing of the connector includes spaced apart disc or shoulder plates 44 and 46 which embrace and engage opposing sides of the wall 24 as the connector is inserted in a slot 48 therein. This secures the connector in place against movement either inward or outward of the housing. The elastic bladder 26 is stretched and mounted between barbed connectors 38 and 42.

The connector assembly 40 preferably includes a luer check valve of a type for such fittings normally available from the Halkey-Roberts, Company of St. Petersburg, Fla. The valve (not shown) is a one way check valve to prevent outflow until a luer connector is mounted on the outlet end of the connector which acts to release or unseat the valve.

The housing may be constructed of any number of suitable engineering thermo forming materials such as, acrylonitrile butadiene-styrene (ABS), polyvinylchloride (PVC), polyethylene terephthalate (PET), polyethylene terephthalate glycol (PETG) and the like. These are well-known lightweight plastics and are materials approved for medical devices.

The tubular member 26 is preferably constructed of an inner tube or sleeve of an inert elastomer and an outer highly elastic tube or sleeve. A preferred rubber material for the inner sleeve is a class of thermoplastic rubber sold under the mark KRATON by Shell Chemical Company of Houston, Tex. These materials are available as KRATON D and G 2000 series rubber, and have FDA status for use in certain applications or ingredients of articles for food contact. These materials are biocompatable and have less than optimum elastic characteristics, and are referred to herein as semi-elastic. When stretched, they initially return to a position of about 75 to about 90 percent of original configuration over a reasonable period of time.

The outer sleeve is preferably made of a natural or synthetic highly elastic rubber such as latex, silicone or other rubber with excellent elastic characteristics, and are referred to herein as elastic. A material with good elastic characteristics returns quickly from a stretched condition to its original un-stressed or un-stretched condition. A good elastic material also has a uniform elastic force over the range stretched and returns substantially all energy put into it. A good elastic rubber can stretch in the range of five hundred to eight hundred percent (500-800%) and return most of the energy as it returns to its original position. Natural latex rubbers are a preferred material for the outer sleeve of tubular member 26. However, certain other rubbers such as silicone rubber would also be suitable.

Referring to FIG. 4, an alternate modification is illustrated which enables a filling of the elastic bladder 26 at the inner end. As illustrated in FIG. 4(a), a fitting 50 has a barbed nipple 52 on which the end 28 of the bladder 26 fits and is secured. The fitting 50 is tubular with a fluid passage 54 communicating with an upwardly extending tubular portion 56 having an elastomeric cap 58. This cap and the passage 56 are aligned with a needle aperture 60 formed in the cover 14 to enable the insertion of a needle or the like for filling the bladder. This also provides an inlet for the addition of medication or drug to an already filled bladder. The fitting is provided with the usual shoulder member 62 for engaging and retaining against the shoulders of the inner extending wall 34, 36.

The elastic tubular member 26 is preferably multiple layer and formed of an extruded biocompatable thermoplastic elastomer or thermoplastic rubber such as described above, that is overformed with a suitable elastic material such as natural or synthetic rubber, such as latex as illustrated in FIG. 5. The KRATON thermoplastic rubbers are medically approved, chemically resistant biocompatable polymers that are semi-elastic. In an exemplary method of manufacturing (FIG. 6) an extruded thermoplastic rubber tubing 26a is extruded from an extruder 64, passed through a liquid bath 66 of highly elastic rubber such as latex several times (up to about twenty) and allowed to set up (polymerize) to form a uniform outer layer or tube 26b of highly elastic rubber.

The tubing moves vertically upward a sufficient height to partially cure before being guided back down into the bath for another coat of the latex. The tubing may be supported on and guided by rollers. The inner tubing is preferably about 15 to 30 thousand (0.015-0.030) of an inch thick and the total thickness is about one tenth (0.1) of an inch. This provides an elastic bladder structure that has a chemically resistant inner lining and a highly elastic outer covering. The combination is more elastic than the KRATON rubber, and has the desired chemical resistance or inertness of KRATON rubber.

The double layer tube may be constructed with a wide variety of other elastic thermoplastic synthetic rubbers including silicone. Most of these would be applied onto the inner tube 26a by a co-extrusion process, as schematically illustrated in FIG. 7. A supply of KRATON rubber is fed from a supply 68 into a die 70 for forming the inner tube. The inner tube is continued through the die where a quantity of elastic rubber from supply 72 is being supplied to the die for the coextrusion of a double layer tube 26.

The configuration of the housing makes the device reasonably compact for its contained fluid volume. The configuration of the elastic bladder pre-stretched on its support structure results in the pressure remaining substantially constant within the unit. The spiral chamber formed by the housing extending outward from the inner end of the wall 18 is preferably of a substantially constant spacing between the walls. The advantage of the prestretch of the elastic tubular bladder is that it flattens the tube against the wall which helps to expel substantially all solution therefrom. Only a small volume of solution is left after infusion. This is typically at a lower pressure than the normal infusion and can result in a small pressurized flow resulting in a "keep-vein-open" mode (KVO). This keeps the infusion site to the vein of the patient open if the bladder is left on past the normal infusion period.

The elastic bladder in a preferred configuration is such that it begins to expand upon filling at one location and expands to the substantially full volume of the chamber in that location, and then extends the filled diameter from one end to the other. The bladder also empties in a reverse manner. With this condition, the housing may be provided with indicia or visual indication of volume to be infused or expelled. These may be in the form of ml markings along the length of the spiral chamber. The infusion apparatus is filled and emptied from the luer connection or fitting 40.

Figure 8:
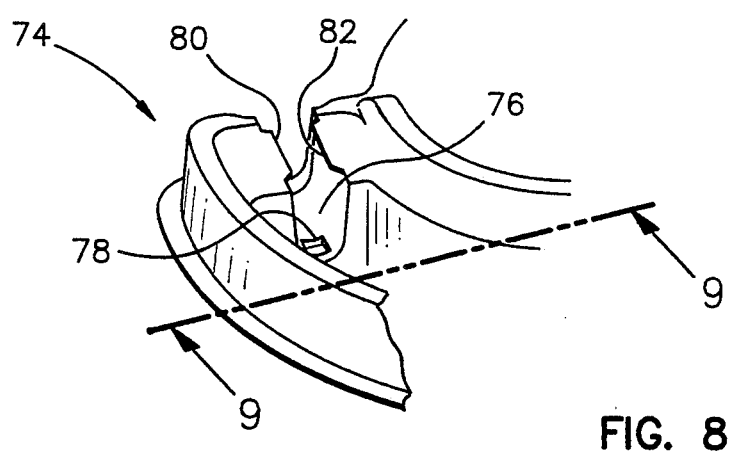
FIG. 8 is a perspective detailed partial view of a modification of the valve mounting portion of the housing of the embodiment of FIG. 1.
Figure 9:
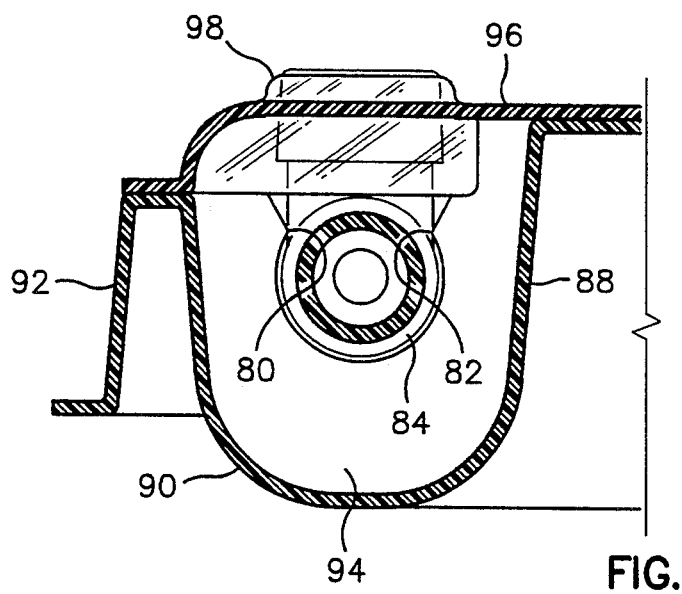
FIG. 9 is a view taken generally on line 9—9 of FIG. 8.
Figure 10:
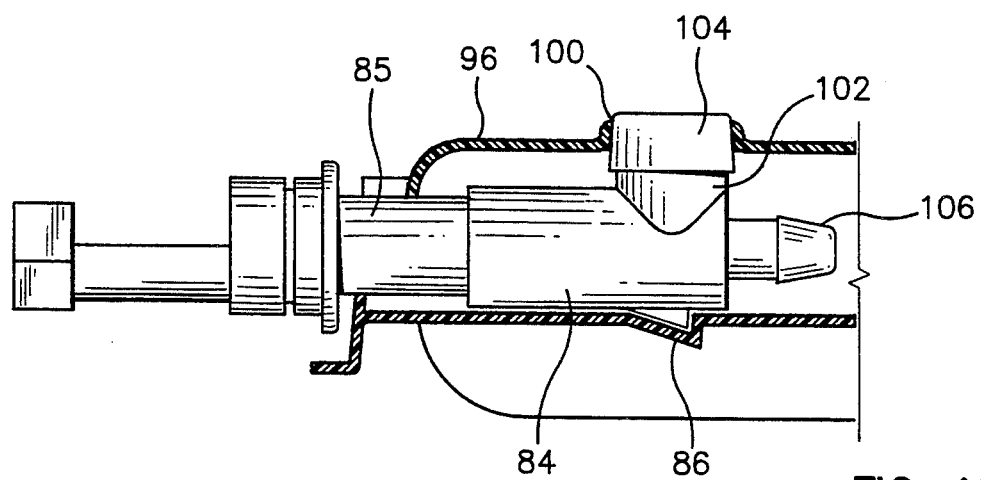
FIG. 10 is a side elevational view partially in section of the structure of FIG. 9.

Referring to FIGS. 8 through 10, a modification to the housing to accommodate a combined filler and delivery valve assembly is illustrated. As illustrated in FIG. 8, the terminal wall area of the housing is molded to form a check valve mounting cradle or recess designated generally at 74 and comprises a semi-cylindrical recess 76 extending from the interior of the housing to the exterior and open at the top of the housing. As more clearly shown in FIG. 9, the cavity or cradle has a flared opening at the top intersecting the cylindrical cavity forming a pair of snap-retaining shoulders 80 and 82 for retaining a valve body 84 in place. The cradle or cavity is formed with a ramp or wedge shaped notch 78 in the bottom thereof for receiving a similarly shaped retaining lug or projection 86 on the bottom of the valve body. The lug and notch retains the valve body in place against the force of the elastic bladder to prevent the bladder from pulling the valve into the housing.

The illustrated housing portion is slightly different in construction than that illustrated in previous embodiments. The housing is formed with spiral supported chamber as in the previous embodiment with an inner wall 88 and an outer wall 90 and with a skirt 92. The spiral chamber in the housing terminates at terminal end wall 94 into which the valve cradle assembly is formed. A cover 96 is preferably formed integral with the main body connected and hinged thereto by means of a live hinge (not shown) on the opposite side of the housing from the valve cradle. The cover is formed with a raised shoulder portion 98 surrounding an opening 100 through which the top of the valve assembly projects. The shoulder portion 98 of the cover engages an upper portion of the valve assembly to aid in retaining the valve in place.

Figure 11:
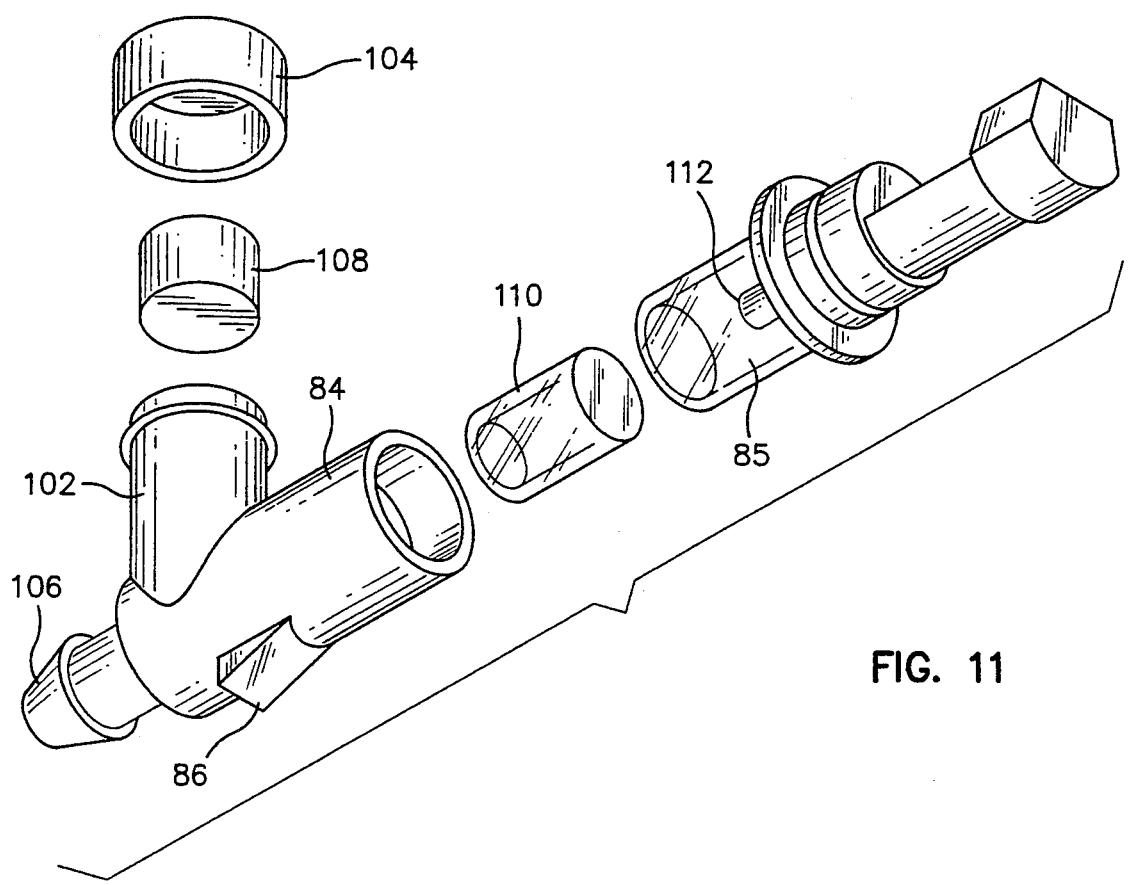
FIG. 11 is an exploded assembly view of the valve assembly of FIG. 10.

Referring to FIG. 10, a side elevation view of the valve and cradle assembly of FIG. 9 is illustrated partially in section showing the valve body 84 and valve assembly in place in the cradle. The valve body as seen in FIG. 11, is a two-part structure with a central portion including a T-juncture 102 branching off at 90° from the main body portion and extending vertically with an injection or fill port structure having an elastomeric stopper or disc 108 retained in place by a cap 104. The cap has an opening in the top to permit access to the elastomeric disc by a needle.

The main body 84 is tubular and contains a silicone valve body 110 of the type previously described, together with a elastomeric disc 112 within a forward body portion 85 forming a spike port connector. This forms a well-known type connection to a tube set, not shown. The main valve body is formed at the opposite end with a barb connection 106 to which one end of the elastomeric bladder is attached.

In operation, the infusion apparatus is filled with a fluid to be infused into a patient. The FIG. 1 and 2 apparatus is filled by connecting the connector 40 to a suitable source of pressurized fluid. As the bladder is being filled, it inflates in response to the pressurized fluid. The inflated bladder retains the fluid under pressure until it is expelled.

The filled infusion apparatus is connected to an infusion site of a patient by a suitable tubing set. This tubing may contain any of a variety of flow restrictions to extend the time over which the fluid is delivered. The pressurized elastic bladder forces the fluid under pressure into the patient until it is substantially empty. The bladder retains a small volume of fluid under lower pressure which can act to keep the infusion site to the vein of the patient open past the usual infusion period.

The FIG., 8–10 apparatus may be filled such as by a syringe connected by a needle to fill port 108. When filled, the needle is removed and the elastic plug 108 self seals. The apparatus is then connected to an IV site of a patient and the pressurized fluid allowed to flow into the patient.

While I have illustrated and described my invention by means of specific embodiments, it is to be understood that numerous changes and modifications may be made therein without departing from the spirit and scope of the invention as defined in the appended claims.

I claim:

1. An apparatus for dispensing a liquid under pressure at a substantially constant flow rate over a period of time comprising:
   support means extending from a central axis with a substantially radial spiral configuration outwardly from said central axis to a terminal end;
   a pressure reservoir defined by an elongated elastic sleeve mounted on said support member and having an inner end disposed at said central axis and an outer end at said terminal end for holding a liquid in a pressurized state for dispensing therefrom;
   means at said outer end for introducing a liquid into said pressure reservoir and for dispensing liquid from said pressure reservoir to a selected site.

2. An apparatus for dispensing a liquid under pressure according to claim 1 wherein said elastic sleeve is pre-stretched onto said support means.

3. An apparatus for dispensing a liquid under pressure according to claim 1 wherein said elastic sleeve is formed of an inner layer of chemically inert thermoplastic rubber and an outer layer of highly elastic rubber.

4. An apparatus for dispensing a liquid under pressure according to claim 3 wherein:
   said support member is defined by an inner wall of a housing; and
   said elastic sleeve is sealingly clamped at an inner end thereof to an anchoring member.

5. An apparatus for dispensing a liquid under pressure according to claim 1 further comprising a housing having an inner wall defining said support means.

6. An apparatus for dispensing a liquid under pressure according to claim 5 wherein said support member extends over at least 270 degrees about said central axis.

7. An apparatus for dispensing a liquid under pressure according to claim 6 wherein said reservoir has a common inlet and outlet.

8. An apparatus for dispensing a liquid under pressure according to claim 7 wherein said reservoir has an inlet at said inner end and an outlet at said outer end.

9. An apparatus for dispensing a liquid under pressure according to claim 1 wherein:
said support member is defined by an inner wall of a housing; and
said elastic sleeve is sealingly clamped at an inner end thereof to an anchoring member.

10. An apparatus for dispensing a liquid under pressure according to claim 9 wherein said reservoir has a common inlet and outlet.

11. An apparatus for dispensing a liquid under pressure according to claim 9 wherein said reservoir has an inlet at said inner end and an outlet at said outer end.

12. An apparatus for dispensing a liquid under pressure according to claim 1 wherein said elastic sleeve is formed of an inner tube of chemically inert thermoplastic rubber formed by extrusion and an outer layer of highly elastic rubber formed on said inner tube by passing same through a bath of liquid rubber.

13. An apparatus for dispensing a liquid under pressure according to claim 1 wherein said elastic sleeve is formed of a coextrusion of an inner tube of chemically inert thermoplastic rubber and an outer layer of highly elastic rubber formed on said inner tube.

14. A dispensing apparatus for dispensing a liquid under pressure at a substantially constant flow rate over a period of time comprising:
a housing having an opening;
support means in said housing having an inner end and a substantially radial spiral configuration outwardly from a central axis to an outer end at said opening;
an elongated elastic sleeve mounted on said support member having an inner end disposed at said central axis and an outer end at said opening for holding a liquid in a pressurized state for dispensing therefrom;
means at said outer end for introducing a liquid into said pressure reservoir and for dispensing liquid from said pressure reservoir to a selected site.

15. A dispensing apparatus according to claim 14 wherein said elastic sleeve is prestretched onto said support means.

16. A dispensing apparatus according to claim 15 wherein said elastic sleeve is formed of an inner layer of semi-elastic thermoplastic rubber and an outer layer of highly elastic rubber.

17. A dispensing apparatus according to claim 16 wherein:

said support member is defined by an inner wall of said housing; and
said elastic sleeve is sealingly clamped at an inner end thereof to an anchoring member.

18. A dispensing apparatus according to claim 17 wherein said support member extends from about ¾ turn to about 2 turns about said central axis.

19. A dispensing apparatus according to claim 16 wherein said reservoir has a common housing having an inlet and an outlet, the outlet being controlled by a check valve.

20. A dispensing apparatus according to claim 16 wherein said reservoir has an inlet at said inner end for introducing a liquid therein.

21. A dispensing apparatus for dispensing a liquid under pressure at a substantially constant flow rate over a period of time comprising:
a housing having a spiral configuration with an outer terminal wall and an opening in said wall;
a support member defined by an inner wall in said housing having an inner end and a substantially radial spiral configuration extending outwardly from said inner end at a central axis to an outer end at said opening;
an elongated elastic sleeve mounted in a stretched condition on said support member and having an inner end disposed at said central axis and an outer end at said opening for holding a liquid in a pressurized state for dispensing therefrom; and
coupling means including a check valve at said outer end for introducing a liquid into said pressure reservoir, and for dispensing liquid from said pressure reservoir to a selected site.

22. A dispensing apparatus according to claim 20 wherein said elastic sleeve is formed of an inner layer of semi-elastic biocompatable elastomer and an outer layer of highly elastic rubber formed on said inner layer; and
said elastic sleeve is sealingly clamped at an inner end thereof to an anchoring member.

23. A dispensing apparatus according to claim 22 wherein said housing has a spiral configuration and said support member extends between about 270° and about 720° about said central axis.

24. A dispensing apparatus according to claim 19 wherein said reservoir has inlet means at said inner end.

25. An apparatus for dispensing liquid under pressure according to claim 3 wherein said inner layer is formed by an extrusion, and said outer layer is formed on an overlayer on said inner layer.

26. A dispensing apparatus according to claim 20 wherein said inner layer is a tube formed by extrusion, and said outer layer is an overlayer formed by passing said tube through a bath of latex.

* * * * *